(12) United States Patent
Raval

(10) Patent No.: US 7,258,236 B2
(45) Date of Patent: Aug. 21, 2007

(54) METHODS AND DEVICES UTILIZING ADSORPTION OF CHIRAL MOLECULES AT A SURFACE OR INTERFACE

(75) Inventor: Rasmita Raval, Liverpool (GB)

(73) Assignee: The University of Liverpool, Liverpool (GB)

(*) Notice: Subject to any disclaimer, the term of this patent is extended or adjusted under 35 U.S.C. 154(b) by 0 days.

(21) Appl. No.: 10/996,262

(22) Filed: Nov. 23, 2004

(65) Prior Publication Data
US 2005/0136195 A1    Jun. 23, 2005

Related U.S. Application Data

(63) Continuation of application No. PCT/GB03/02271, filed on May 23, 2003.

(51) Int. Cl.
*B03C 1/02* (2006.01)
*B01D 15/08* (2006.01)
*B01D 35/06* (2006.01)

(52) U.S. Cl. ............... 209/8; 210/222; 257/E51.023; 369/13.02; 977/838

(58) Field of Classification Search .............. 209/8; 210/222; 257/E51.023; 349/23; 369/13.02, 369/97.02; 977/838
See application file for complete search history.

(56) References Cited

U.S. PATENT DOCUMENTS 6,106,724 A * 8/2000 McCulloch et al. ........ 210/656

6,313,247 B1 * 11/2001 Lindner et al. ............. 526/259
6,316,235 B1    11/2001 Mosbach et al.
2002/0004608 A1 * 1/2002 Alig et al. .................... 560/22

FOREIGN PATENT DOCUMENTS

EP    0 758 803 A1    2/1997

OTHER PUBLICATIONS

Carmeli et al., "Magnetization of Chiral Monolayers of Polypeptide: A Possible Source of Magentism in Some Biological Membranes", Angewandte Chemie, 41(5), 761-764, 2002).*
Norbert M. Maier, Pilar Franco and Wolfgang Lindner, *Separation of Enantiomers: Needs, Challenges, Perspectives*, Journal of Chromatography, vol. 906, No. 1-2, Jan. 12, 2001, pp. 3-33, Elsevier Science Publishers B.V. Amsterdam, NL.
International Search Report dated Aug. 28, 2003.
International Preliminary Examination Report dated Jan. 15, 2004.

* cited by examiner

*Primary Examiner*—Shean C. Wu
(74) *Attorney, Agent, or Firm*—Patterson & Sheridan, L.L.P.

(57) ABSTRACT

The present invention is concerned with the adsorption of chiral molecules at surfaces or interfaces, with the arrangement and properties of adsorbed chiral molecules, and with devices and methods based thereupon. In particular, an apparatus allows the influence of the magnetic environment of the adsorbed chiral molecules by means of a magnetic field. The new observed orientation of the adsorbed chiral molecules caused by the chiro-magnetic effect, and the possible applications, are disclosed too.

82 Claims, 7 Drawing Sheets

Fig. 2
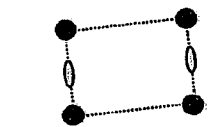
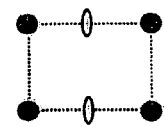
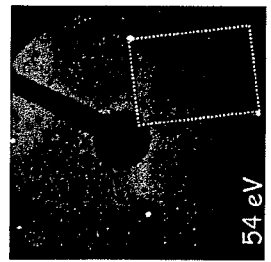
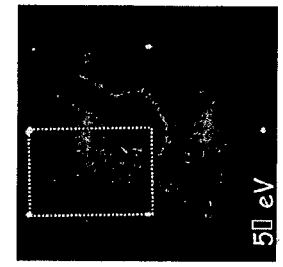
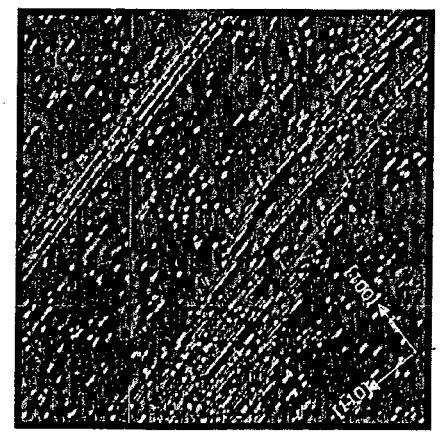
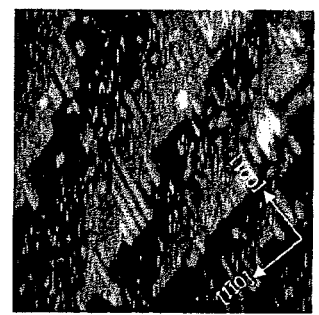
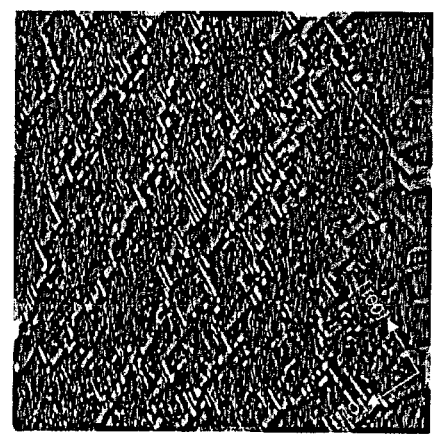

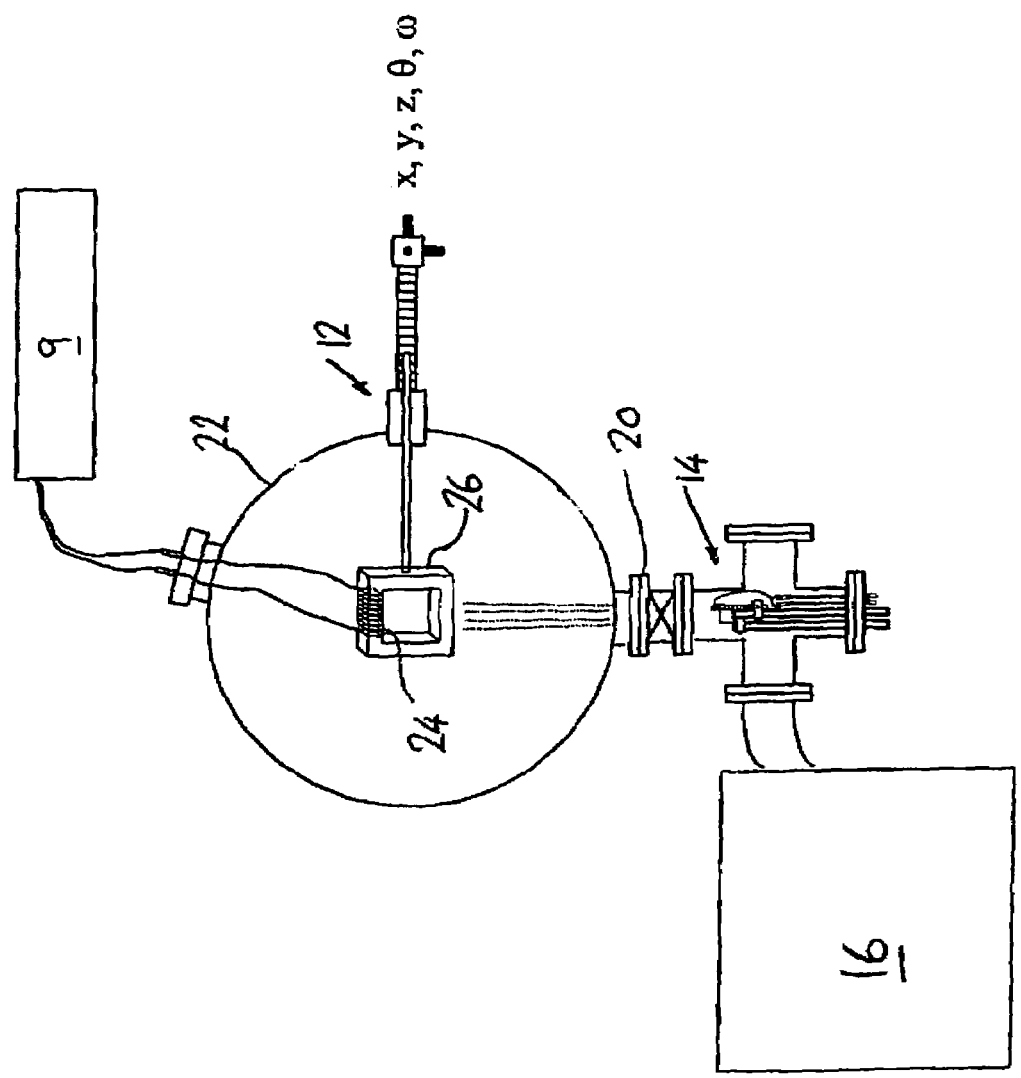

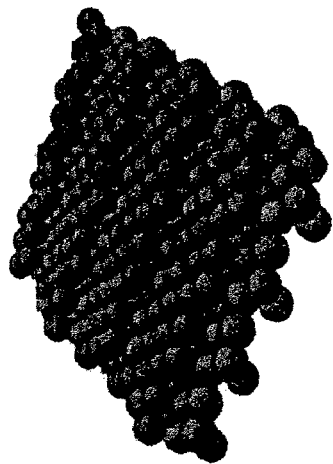
fcc(643)^R
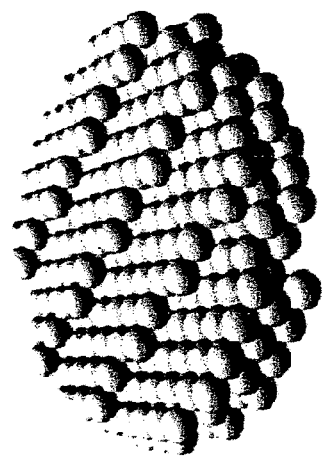
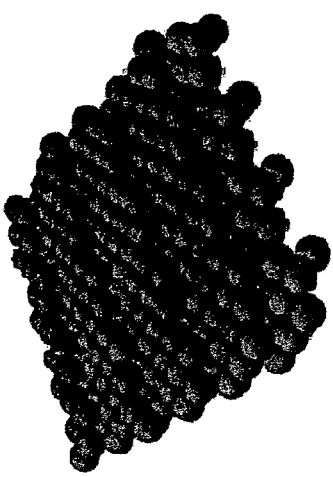
fcc(643)^S
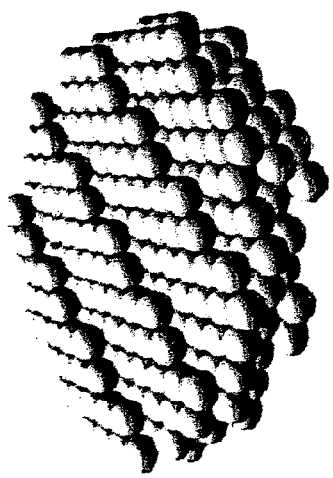
Figure 9

METHODS AND DEVICES UTILIZING ADSORPTION OF CHIRAL MOLECULES AT A SURFACE OR INTERFACE

CROSS-REFERENCE TO RELATED APPLICATIONS

This application is a continuation of co-pending PCT patent application No. PCT/GB03/02271, filed 23 May 2003, which claims the benefit of GB patent application Ser. No. 0211931.1, filed 23 May 2002. Each of the aforementioned related patent applications is herein incorporated by reference in their entireties.

BACKGROUND OF THE INVENTION

1. Field of the Invention

The present invention is concerned with the adsorption of chiral molecules at surfaces or interfaces, with the arrangement and properties of adsorbed chiral molecules, and with devices and methods based thereupon.

2. Description of the Related Art

The technological and scientific use of chiral molecules is widespread [1]. In contrast, the use of adsorbed chiral molecules at surfaces is, at present, much more restricted and includes applications in heterogenous enantioselective catalysis [see references 2-9, listed below], where the process allows the production of specific enantiomers for commercial use, e.g., in the hydrogenation of -ketoesters. In these applications the role of the adsorbing chiral molecule is to bestow chirality to the chiral surface. There is also only a small volume of fundamental scientific literature [e.g., references 10-20] explaining the observed behavior of adsorbed chiral molecules at non-chiral surfaces and interfaces. This shows that chirality can be introduced to the surface in a number of ways ranging from local chiral adsorption [10, 16, 19] to self-organization in chiral domains [10-12, 14, 15], to local chiral reconstructions [10, 18, 19]. It is known that non-chiral molecules adsorbed on a non-chiral surface can give rise to local chirality within an overall racemic system [e.g., 17, 18, 20]. Therefore the utilization of chiral adsorbing molecules is important in creating complete chirality at the surface, however for certain applications it may be sufficient to work with locally chiral systems.

In all recorded cases known to the inventors where surface chirality is observed, adsorption of an enantiomer and its twin would lead to adsorption where each is aligned symmetrically on either side of a geometric mirror plane [10, 11, 17]. An example is the adsorption of R, R-Tartaric acid and S, S-Tartaric acid on Cu (110) single crystal surface, see reference [11] and also FIG. 1, in which can be seen the orientations of single monolayers of enantiomers of tartaric acid on Cu (110). Molecules of different enantiomers orient themselves symmetrically with respect to a geometric mirror plane of the Cu substrate.

When repeating the experiment on the more commercially relevant Ni (110) surface, it was surprisingly found that the alignment and growth direction of the two R,R-tartaric acid and S,S-tartaric acid enantiomers were perpendicular to each other in directions not related by any geometric mirror plane possessed by the bare surface. Experimental details are provided below. There was no obvious explanation for this observation since all previous work had predicted a geometrically symmetrical arrangement. This new phenomenon which had been discovered could not be explained on purely geometric grounds and can only be understood in terms of a magnetic effect in which the magnetization and spins of the surface influence, and are in turn influenced by, the adsorption of the chiral molecule. Detailed ab initio calculations of the molecule/metal system, which included magnetic effects, have been made to confirm that the adsorption and bonding of a chiral molecule at the surface is, in fact, affected by the inherent magnetization of the surface. In particular the chirality of the molecule dictates which surface spin states are involved in the adsorption and bonding process, an effect that has never been proposed nor observed before. Although the connection between chirality and inherent magnetism has been documented [21-25], e.g., for molecules, metal-molecule complexes, bulk solid state compounds and carbon nanotubes, and has been used to demonstrate enantioselective magnetochiral photochemistry in solution, it has never been observed or proposed for adsorbed molecules at surfaces. This effect is also manifestly different to the reported work on chiral monolayers of polypeptides adsorbed at a surface where very large external magnetic fields were applied subsequent to the adsorption process in order to induce the long, polymeric non-bonding pendant chains to take up different orientations, according to a chirality of the helix, the time that the field is applied and the packing density of the monolayer [26].

SUMMARY OF THE INVENTION

Various applications of the newly observed phenomenon have been devised.

In accordance with a first aspect of the present invention there is an apparatus or device comprising chiral molecules and a surface or interface at which the chiral molecules are capable of being adsorbed, wherein the adsorption of the molecules is influenced by their magnetic environment in a manner which is different for two different enantiomers thereof.

The invention may be embodied in apparatus, e.g., for manufacture and research, or in devices such as logic devices and enantio-selective filters.

The invention encompasses both apparatus/devices in which the molecules are adsorbed at the surface during manufacture, and in which the molecules become adsorbed at the surface during operation.

Here, the term surface includes extended surfaces or films or surfaces of nanoparticles. Suitable adsorption in question may be at an interface between two separate entities. The adsorbing surface materials include, but are not limited to, metal, semiconductors, oxides, organic conducting films, alloys and composites. The adsorbing surface materials may comprise one or more selected from the group comprising of non di-magnetic material, iron, cobalt and platinum.

Molecules which can be used in these applications include but are not limited to all forms of chiral molecule including without limitation all chiral organic molecules, sugars, nucleotides, polynucleotides, amino acids, peptides, polypeptides, proteins, inorganic molecules and complexes and indeed any molecule which is not inherently chiral but becomes chiral by virtue of being adsorbed on a surface. The word "chiral" as used herein must be understood to include molecules which exhibit chirality by virtue of adsorption, as well as molecules which are inherently chiral. The effect is expected to be greatest for molecules with unpaired electrons (e.g., carboxylates, nitrosyls, nitroxides), radicals, compounds with high spin, organometallics and molecular magnets.

It is expected that the effect can be enhanced by using ultra small particles, e.g., nanoparticles, or by using a strained surface such as a metallic film grown upon another substrate having different dimensions.

The influence of the molecule's magnetic environment is different in magnitude for the different enantiomers. The inventors have demonstrated that magnetic influences are responsible for an angular displacement of the molecules which is different in magnitude for the two different enantiomers. This magnetic influence may affect the energy balance involved in bonding of the chiral molecules to the surface. Hence another result of such influence is that in some devices embodying the present invention adsorption of one enantiomer may be favored over adsorption of the other.

The adsorption of the chiral molecules may be due to chemical adsorption (chemisorption), such as chemical bonding, e.g., covalent bonding, or due to physical adsorption (physisorption), e.g., via weaker interactions, such as the Van der Waals force.

The device may be (but is not necessarily limited to) a filter, an electronic/spintronic device or a sensor.

In accordance with a second aspect of the present invention there is an apparatus comprising a substrate providing a surface or interface, means for providing a magnetic field at the surface or interface, and means for supplying chiral molecules for adsorption at the surface or interface, the adsorbed molecules being influenced by the magnetic field in a manner which is different for different enantiomers thereof.

In accordance with a third aspect of the present invention there is a method comprising controlling at least one property of chiral molecules adsorbed at a surface or interface by controlling the molecules' magnetic environment.

In accordance with a fourth aspect of the present invention there is a method of analysis, separation or manufacture in which chiral molecules are adsorbed at a surface and the adsorption or desorption of the molecules is influenced by their magnetic environment in a manner which is different for two different enantiomers of the chiral molecules.

In accordance with a fifth aspect of the present invention there is a method of manipulating the magnetization of a body providing a surface or interface comprising adsorption thereupon of chiral molecules.

The method may comprise selecting an enantiomer to be adsorbed. The method may involve use of two different enantiomers and arranging for selective adsorption or desorption of one or other of them.

The effect of adsorption of the chiral molecules is believed to be to alter spin states of the material of the surface or interface.

Application of known techniques allows the location of adsorption of the chiral molecules to be selected in order to allow localized manipulation of the magnetization of the surface or interface. Hence in a further preferred embodiment of this aspect of the present invention the manipulation of the magnetization is localized. Such localization can be from a microscopic to a molecular level.

In accordance with a sixth aspect of the present invention there is a device for manipulating magnetization comprising a body providing a surface or interface, chiral molecules adsorbable thereupon and means for controlling adsorption of the molecules on the surface to thereby manipulate magnetization at the surface.

Preferably the device further comprises means for localizing the adsorption of the chiral molecules.

The device may comprise a logic device and more specifically may comprise a memory. In such a device the chiral molecule may be used to switch spin states of the body. By interpreting spin states as logic states, a high density memory may thereby be manufactured.

In accordance with a seventh aspect of the present invention there is a logic device comprising a surface or interface and chiral molecules adsorbed thereupon.

In such a device, adsorption or desorption of a chiral molecule on the surface or interface may produce a change in a spin state of the surface or interface, interpreted as a change of logic state.

Additionally or alternatively, the position or orientation of enantiomers in such a device may correspond to logic states, the device further comprising means for switching enantiomer position or orientation. Such means may comprise means for selectively applying a magnetic, electric or electromagnetic field.

In accordance with an eighth aspect of the present invention there is a method of sensing magnetization states at a surface or interface comprising adsorption of chiral molecules at the interface or surface.

The chiral molecule orientation may be detected as an indicator of magnetization. Alternatively since the energy involved in adsorption may be affected by magnetization of the surface or interface, the adsorption or non-adsorption of one enantiomer or the relative rates of adsorption of two enantiomers may be detected as an indicator of magnetization.

The magnetization detected may be highly localized, even to the molecular level.

In accordance with a ninth aspect of the present invention there is a method of separation of enantiomers from a racemic mixture of chiral molecules comprising selective adsorption or desorption of chiral molecules at a surface or interface.

This possibility results from the different energy considerations in adsorption of the different enantiomers, which can result in adsorption or desorption of one enantiomer being favored, or in only one enantiomer being capable of being adsorbed or desorbed. Such a method could further comprise the step of controlling temperature to adjust the rate of adsorption of one or both enantiomers. A selected enantiomer may for example be desorbed by virtue of a rise in temperature.

In accordance with a tenth aspect of the present invention there is a separation medium for separating different enantiomeric forms of a chiral molecule, comprising a surface upon which at least one enantiomer is adsorbable, the rates of adsorption of the different enantiomers on the surface being different.

In accordance with an eleventh aspect of the present invention there is a method of nanopatterning or lithography comprising adsorption of chiral molecules at a surface or interface and controlling a local magnetic field to control said adsorption. In this way a controllable pattern or array may be created. The method preferably involves control of chiral molecular orientation by control of the molecules' magnetic environment.

In accordance with a twelfth aspect of the present invention there is a method of heterogeneous catalysis in which chiral molecules are formed by reactions taking place at a surface or interface, the formation of a selected enantiomer being promoted by influencing the magnetic environment of the surface.

In accordance with a thirteenth aspect of the present invention there is a device comprising chiral molecules and a surface or interface at which the chiral molecules are adsorbed, the surface or interface being ordered such as to have a mirror plane, wherein the adsorbed chiral molecules align themselves in an ordered manner, the orientations of different enantiomers of the chiral molecules being asymmetric with regard to any mirror plane of the surface or interface.

The surface or interface is most typically crystalline.

A symmetrical difference between the two enantiomers would for example imply that, in the case of molecules being adsorbed on a crystalline surface having a mirror plane, the two enantiomers would be equally but oppositely angularly displaced about a mirror plane of the crystal. The inventors have demonstrated an asymmetric magnetic influence, as a result of which the two enantiomers are not symmetrically arranged about any mirror plane of a crystal.

While in the aforegoing aspects of the present invention the magnetic fields influencing adsorption of the chiral molecules may arise wholly or principally from the spins at the surface or interface, the device or method may additionally be influenced by application of an external magnetic field or by bulk magnetization of material providing the surface or interface, or indeed by magnetization of the material on a smaller scale, e.g., in the magnetic domains of a ferromagnetic material.

Furthermore, in the aforegoing aspects of the present invention, where adsorption or desorption of the chiral molecules is influenced by their magnetic environment in a manner which is different for two different enantiomers of the chiral molecules, the manner in which they are influenced may be non symmetrical.

BRIEF DESCRIPTION OF THE DRAWINGS

Specific embodiments of the present invention will now be described, by way of example only, with reference to the accompanying drawings in which:

FIG. 2a-b both contain two scanning tunneling electron microscope images and FIG. 2c contains two Low Energy Diffraction patterns, each showing, respectively, right and left handed tartaric acid molecules adsorbed upon a crystalline nickel surface;

FIG. 4 is a schematic representation of a further apparatus embodying the present invention;

FIG. 9 illustrates the structure of chirally cut surfaces for use in certain embodiments of the present invention.

DETAILED DESCRIPTION OF THE PREFERRED EMBODIMENT

Figure 1:
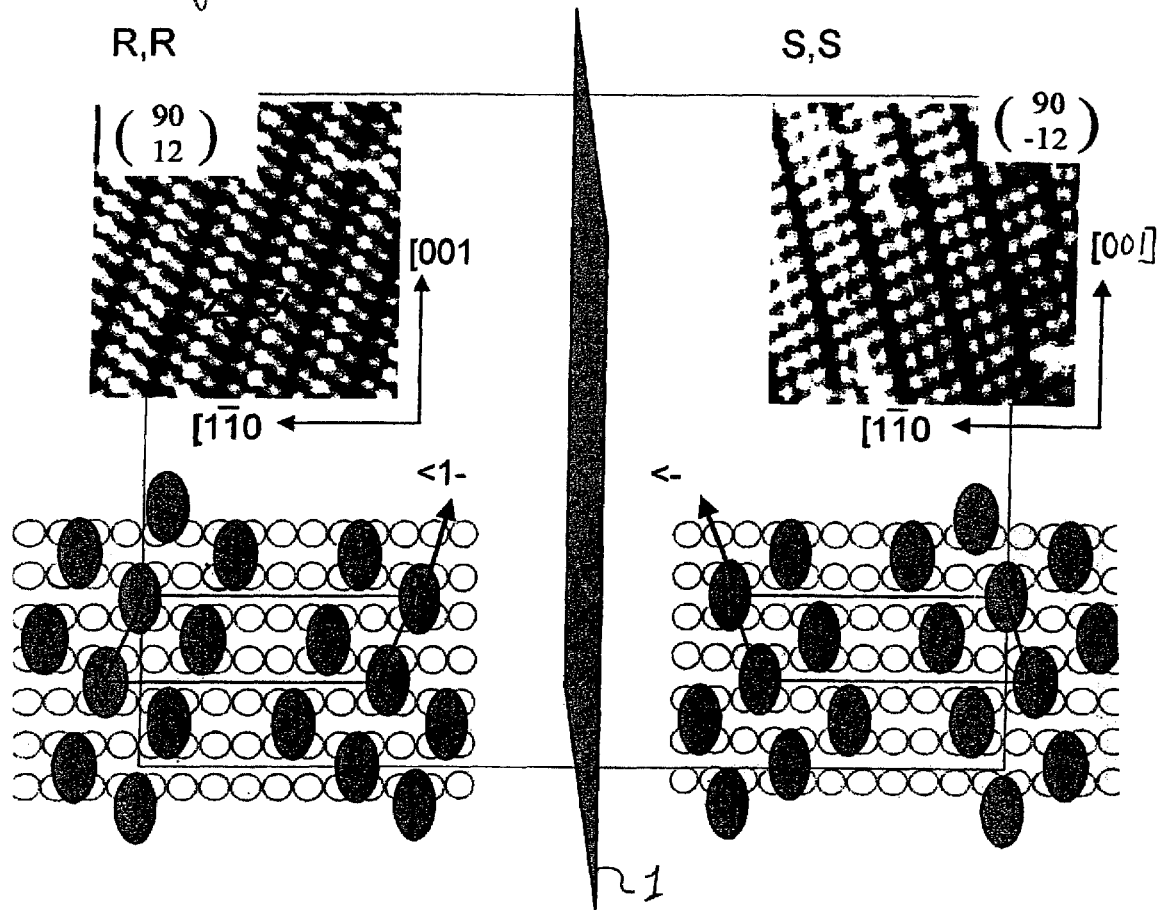
FIG. 1 contains a schematic illustration and images from a scanning tunneling electron microscope of the arrangement of right and left handed surface assemblies created by the adsorption of single monolayers of tartaric acid on Cu (110)

Before considering the experimental findings underlying the present invention, refer to FIG. 1 which shows an example of the behavior of adsorbed chiral molecules which would be expected according to the (hitherto) conventional understanding. At the head of this Figure are scanning tunnelling microscopic images of R,R and S,S enantiomers of tartaric acid molecules adsorbed upon a single crystal [110] copper surface. The schematic representations lower down the Figure are intended to make clear the orientations of the acid molecules. The mirror plane of the crystalline copper substrate is shown schematically at 1. It can be seen that the two enantiomers are symmetrically arranged about the mirror plane. They align at equal but opposite angles with respect to the plane 1.

This is to be contrasted with results from the inventor's experiment demonstrating the newly observed surface chiromagnetic effect, which will now be described.

Experiments were conducted in an ultra high vacuum (UHV) chamber where STM (scanning tunneling microscopy) experiments were conducted in an Omicron Vakuumphysik chamber with facilities for STM, LEED (low energy electron diffraction), AES (Auger Electron Spectroscopy) and sample cleaning.

The nickel crystals were provided by Surface Preparation Laboratory (Netherlands) with purity of 99.99% (4N), and alignment accuracies of 0.1 for the STM experiments. The Ni (110) crystal was cleaned by cycles of Ar+ ion sputtering, flashing and annealing at 900K. The surface cleanliness and ordering were monitored by AES and LEED. R, R-tartaric acid (99%) and S, S-tartaric acid (99%) were obtained from Sigma-Aldrich Chemicals and used without any further purification. The required tartaric acid sample was contained in a small resistively heated glass tube, separated from the main chamber by a gate valve and differentially pumped by a turbo molecular pumping system. Before sublimation, tartaric acid was outgassed at 330K, then heated to 370K to cause sublimation and thus be exposed to the nickel crystal. Adsorption experiments for each enantiomer were carried out separately, so data were obtained in separate experiments for the R,R-tartaric acid/Ni(110) system and the S,S-tartaric acid/Ni (110) system. During sublimation the main chamber base pressure was typically $2 \times 10^{-9}$ mbar. The required adsorption phase was created either by exposure of the Ni (110) to the sublimation pressure of the tartaric acid for between 4-10 min with the Ni sample held at 380K, or for the same exposure with the Ni sample held at 300K and then subsequently warmed to 380K to create the required phase. Once the required adsorption phase was created, the sample was recooled to 300K and STM images were acquired in constant current mode.

As explained above, the enantiomers are observed to be oriented in directions not related by any geometric mirror plane of the crystal surface. This is taken as an indication that magnetization of the substrate affects the molecules in a different manner. The magnitude of this effect is larger than would have been predicted based on conventional understanding and is different for different enantiomers. In FIGS. 2(a) and (b), the [110] and [001] mirror planes of the crystalline nickel substrate are indicated by arrows and it will be apparent that the orientations of the R,R and S,S enantiomers are not symmetrically arranged about either mirror plane. According to the hitherto accepted understanding, it would have been expected that the two enantiomers would align themselves upon adsorption with equal but opposite angles to a mirror plane. This is not the case in the illustrated example.

This unexpected phenomenon is attributed to the effects of inherent magnetization of the nickel substrate in the illustrated example. However the adsorbed molecules can also be influenced by application of an external magnetic field, as will be further explained below.

The surface for adsorption may be crystalline. However nano-crystalline surfaces are believed to exhibit the effect.

According to the inventor's current understanding, it is the chiral molecules' magnetic environment that causes the asymmetry of molecular alignment and other enantio-selective phenomena to be discussed below. Both macroscopic and microscopic effects contribute to this environment. Thus, in the aforementioned test, bulk and surface magnetization of the nickel substrate—a macroscopic property—is believed to give rise to the asymmetric molecular orientation. An externally applied magnetic field, on a macroscopic scale, can also be used to influence the adsorbed molecules. However at the microscopic scale the phenomenon is believed to depend also upon the interaction of electron spins in the substrate and the chiral molecule.

Important implications of this work include the following:
a) adsorption of the chiral molecule senses the inherent magnetization and spin states of the surface;
b) the adsorbed molecule affects the surface spin states in a manner that is related to the inherent chirality of the molecule;
c) these effects are present and sustained at room temperatures and relate to the large energy differences that come into play due to this surface chiro-magnetic effect; and
d) the cost of selective separation using this effect are considerably less than current chiral technology methods of producing single enantiomers in industry today. This effect, therefore, opens up many technologies to the use of chiral molecules.

Both the nature and the magnitude of this phenomenon is such that it has considerable and wide-ranging commercial implications in technologies that utilise adsorbed molecules at surfaces, including but not limited to,
(i) molecular electronics
(ii) data storage
(iii) heterogeneous enantioselective catalysis
(iv) nanopatterning and lithography
(v) analytical instrumentation or sensors
(vi) separation techniques
(vii) creating cheap selective coatings and barriers.

All these advances are particularly favorable because the effect is observed not only at low temperatures but also at commercially relevant room temperature and may be tuned over a wide temperature range depending on requirements.

Taking each of these in turn, the following is suggested:
(i) In molecular electronics and molecular computing the chiro-magnetic effect can be utilized at a surface to align chiral molecules into a controlled assembly e.g., as molecular wires or other designed surface architectures [27, 28]. In addition, molecular switches, logic gates, etc could be designed that alter positions of enantiomers through the application of an external magnetic field or electric impulse or electromagnetic field or through the adsorption and readsorption of chiral molecules on specific surfaces. Although considerable literature exists on the synthesis of single-molecule magnets [29-36], the effect we observe at surfaces is particularly important since it is present at room temperature whereas previous single-molecule magnetic effects have been restricted to very low temperatures (4-100K) which are not commercially relevant.
(ii) In data storage [37], the chiro-magnetic effect can be used to utilize a single molecule to switch the spin states at a surface giving an unprecedented density of storage. Overall this effect, essentially, enables the molecule to 'write' on a surface.
(iii) In heterogeneous catalysis the effect can be used to enhance the selective production of specific enantiomers through influencing the magnetic environment of the surface. The system can be used to selectively adsorb an enantiomer by virtue of its different adsorption energy or, having adsorbed the molecule, to selectively desorbed a specific enantiomer from a surface by raising the temperature of the surface. Alternatively a racemic experiment can be carried out and the selected chiral product or intermediate be selectively retained or evolved. Such processes could have considerable implications in cheaper and more efficient production of a number of products including, but not limited to, pharmaceuticals, herbicides, pesticides, flavours and fragrances.
(iv) In nanopatterning and lithography it is necessary to lay down molecules in specific orientations. The chiro-magnetic effect can be mediated by influencing the laying down of molecules by controlling the local magnetic field to create a pattern or array.
(v) It is possible to construct analytical instruments or sensors using the effect which utilize the sensitivity of the chiral molecules to magnetic environment. The presence of a docking molecule at the surface would be monitored through a change in the magnetic environment of the chiral molecule giving rise to a detectable output signal.
(vi) The effect can be used to manufacture separation media which selectively separate chiral molecules for use in commercial separation technology including analytical instrumentation. Equally it is possible to carry out chiral separations using the fact that each enantiomer has a different adsorption energy on a specific magnetic surface. Hence selective separations could be carried out by designing the magnetic surface.

The effect has application in the design of special filters for selective filtration of living material such as bacteria or viruses. The effect can be used to coat surfaces to adsorb harmful bacteria or viruses in living organisms or in making surfaces biocompatible.

The present invention provides a method of coating surfaces with selected chiral molecules that is much cheaper, therefore opening up this approach to produce selective coatings and barriers.

The implementation of some of these aspects will be considered in more detail below.

Figure 3:
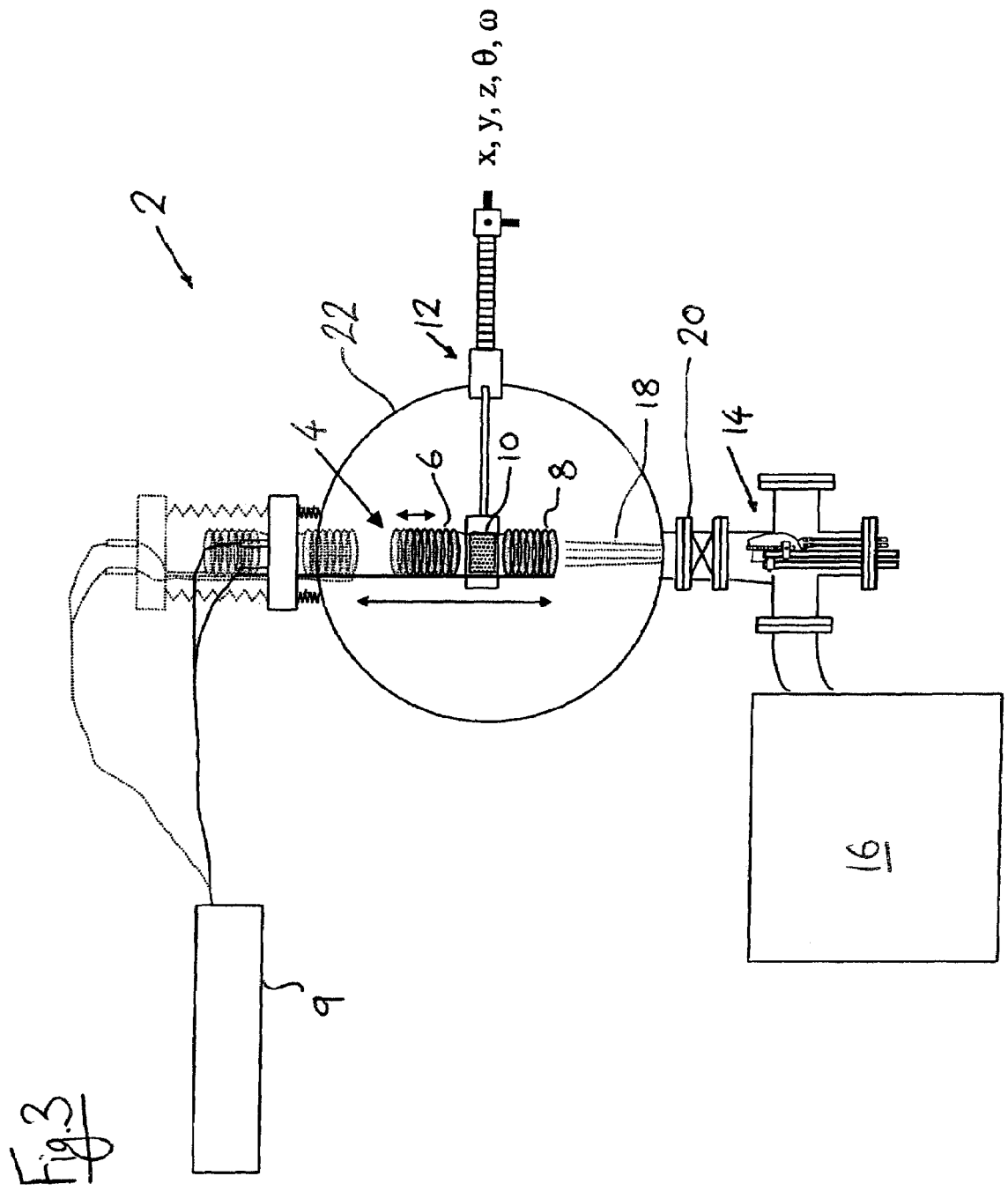
FIG. 3 is a schematic representation of an apparatus embodying the present invention.

FIG. 3 illustrates, in schematic form, an apparatus 2 for use in studying and utilizing the chiro-magnetic effect, comprising an arrangement 4 for applying an external magnetic field to a sample. In the illustrated sample this arrangement uses a pair of magnetic coils 6, 8, which are movable, as suggested by the dotted representation of the coils showing them in an alternative position. The strength and polarity of the magnetic field can be manipulated by selection of the number of magnetic coils, current magnitude (from a power supply 9) and direction, and coil position relative to the sample. It will be apparent to the skilled reader that the magnetic field could be applied using a variety of alternative techniques including but not limited to permanent magnets, electromagnets, superconducting magnets and, high field magnets. The magnetization may be pulsed or continuous. The substrate can be placed in the coil, between coils, directly in the bore of a magnet or indeed in any orientation or position relative to the magnet. For certain trials/applications the external magnetic field may be dispensed with, particularly where the sample is magnetized.

The sample 10 of substrate material is mounted in the magnetic field. In the illustrated arrangements the orientation of the sample is adjustable by means of a manipulator and an azimuthal stage 12, allowing alignment of the sample in any chosen direction (x, v, z, θ, w) with respect to the magnetic field. Heating, cooling and temperature measurement of the substrate are also provided for.

Provision is made for dosing of chiral molecules to the sample for adsorption thereupon. This can be done in a variety of ways. In the illustrated example the chiral molecules are evaporated or sublimed in the gas phase and dosed onto the sample. FIG. 3 shows a sublimation doser 14 pumped by a turbo molecular pumping system 16. The flux of molecules 18 from the doser is output through a gate valve 20 to the sample. The doser may be a multi or single channel device.

The sample is housed within an envelope 22 in which a range of conditions may be created ranging from ultra high vacuum to high pressure conditions.

In use, a chosen enantiomer may for example be dosed on the sample 10, aligning upon its surface according to the previously described chiromagnetic effect in a preferred orientation. The mirror enantiomer may then be dosed and will align in a different orientation even in the same applied field.

FIG. 4 illustrates an arrangement which is very similar to that of FIG. 3. Like components are given the same reference numerals. The two arrangements differ in that in FIG. 4 the magnetic field is applied through windings 24 upon a sample 26 in the shape of a square loop or picture frame.

Figure 5:
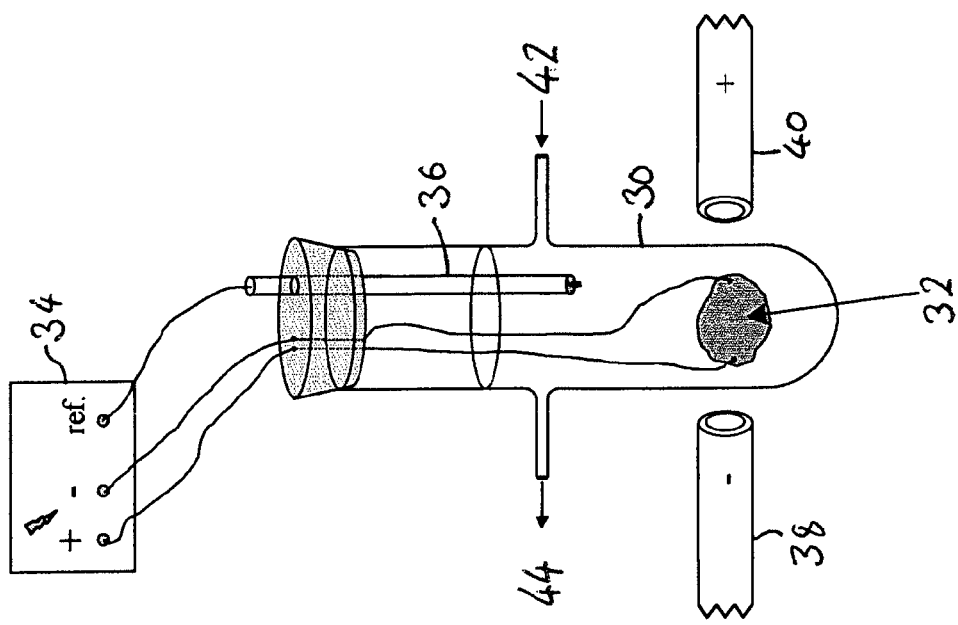
FIG. 5 is a schematic illustration of a further apparatus embodying the present invention.

FIG. 5 illustrates an alternative arrangement in which the chiral material is deposited from the liquid phase. The sample is under electrochemical control, being incorporated in an electrochemical cell such that surface potential can be varied to control adsorption properties. A vessel 30 contains the sample 32 which is immersed in fluid. A supply 34 is electrically connected to the sample and also receives a reference signal from an electrode 36 immersed in the fluid. The magnetic field is applied to the sample by magnets 38, 40 which again may take any of a wide variety of forms. An inlet 42 and outlet 44 allow for a fluid flux through the vessel e.g., for control of concentration of the chiral molecules.

Figure 6:
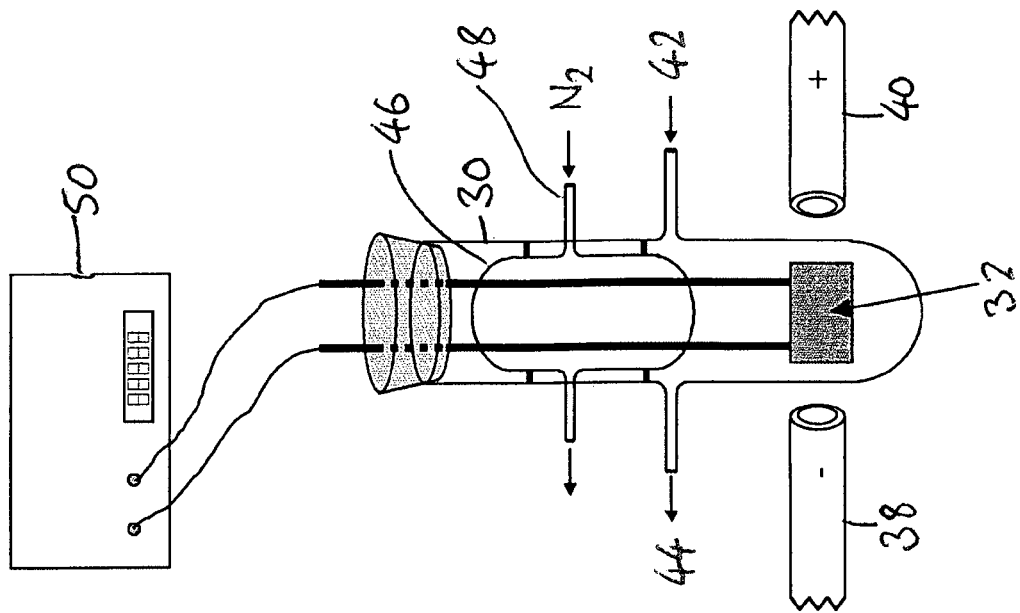
FIG. 6 is a schematic illustration of still a further apparatus embodying the present invention.

The arrangement illustrated in FIG. 6 is similar to that shown in FIG. 5 and like components are given the same reference numerals. However to allow for low temperature operation the vessel 30 contains a chamber 46 connected through inlet 48 to a supply of liquid nitrogen, controlled by a temperature controller 50 connected to the sample 32. The chiral material is again passed into the vessel through an inlet 42 and exhausted at 44, although in this arrangement it is typically in gaseous form.

The present invention is applicable to the manufacture of various devices on a microscopic and on a molecular scale, including molecular wires, molecular switches, microcircuits and nanopatterns.

The manipulation of magnetic field orientation, enantiomer selection and concentration, and position relative to the field during dosing allows an assembly of molecules to be built up in a preferred pattern to form the basis of such devices. Patterning can be achieved by dosing enantiomers in the presence of a gradient magnetic field. The resultant pattern would vary from random to highly aligned depending on the position of the sample at which deposition occurs, and the selected enantiomer in single or multiple dosing. Patterning can also be achieved by creating a surface which is partly masked for the first adsorption creating an aligned enantiomer in a preferred orientation on one part of the surface. Removal of part or all of the mask allows subsequent deposition of the same or different enantiomers in different orientations according to the field position and the enantiomer selected.

Figure 7:
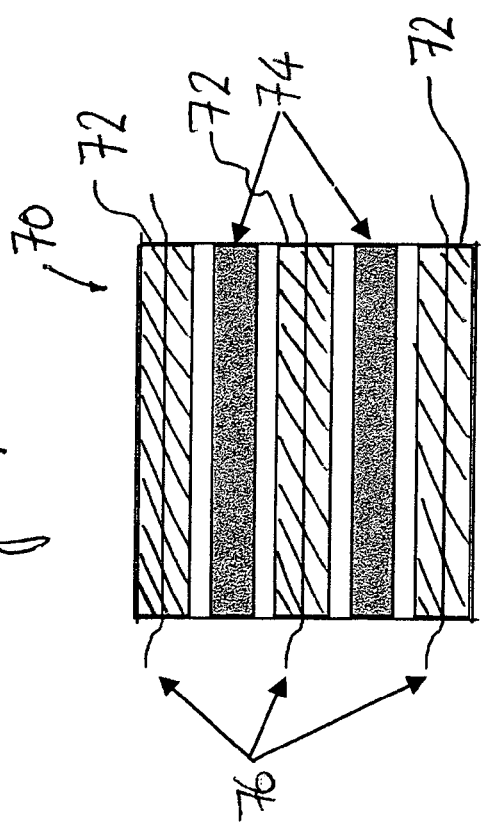
FIG. 7 is a plan view of a substrate for use in embodiments of the present invention.

An alternative means of creating pattern in the adsorbed chiral molecules is illustrated in FIG. 7. Here the chiral material is to be adsorbed upon the uppermost face of a substrate 70 which has a segmented surface structure comprising individual layers 72 of material for receiving the chiral material, each separated from its neighbors by a respective thermal/electrical insulator layer 74. Each receiving layer 72 incorporates a respective electrical heating element 76. Hence chosen sections of the substrate can be heated, thermal effects causing the enantiomer to be desorbed in the chosen sections. The heating may be such as to raise the receiving material above its Curie point, locally scrambling applied magnetization in the chosen sections.

A second, mirror, enantiomer is then dosed which deposits in a different orientation on the available surface. Hence an array of molecules can be built up with specific patterning. Manipulation of the temperature of specific sections may also be used to prevent deposition of specific enantiomers.

Figure 8:
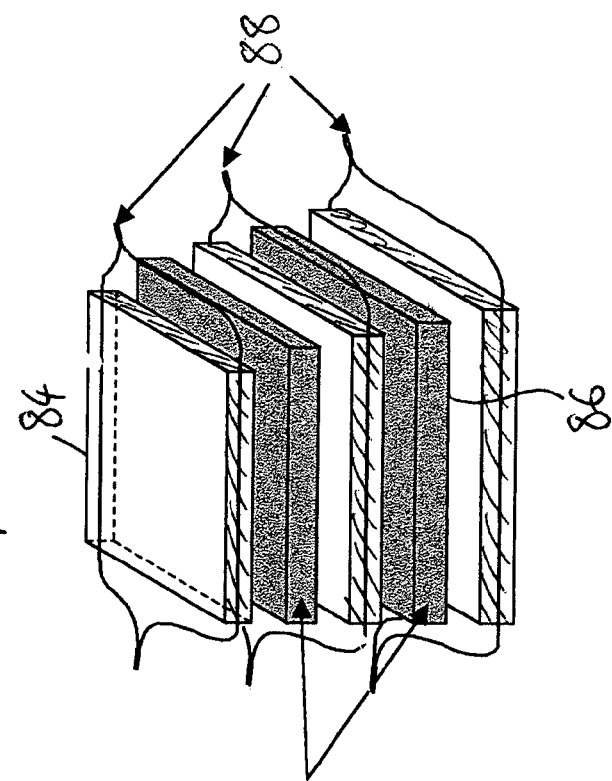
FIG. 8 is a perspective view of a further substrate for use in embodiments of the present invention.

FIG. 8 illustrates a substrate somewhat similar to that of FIG. 7 in which chiral material can be selectively deposited upon chosen planes in a 3-dimensional structure, receiving layers 84 being again separated by insulating layers 86 and individually heated by ohmic heating elements 88.

Patterning may also be achieved by creating a concentration gradient of particular enantiomers across a sample which is either premagnetized or magnetized during deposition. The alignment pattern will depend on the field applied, the selection of enantiomer, the position of the sample and the concentration gradient at a particular point on the sample.

Patterning may be achieved by STM manipulation [37] to deliver molecules to precise surface sites. The technique is well known.

Further, patterning may be achieved by using a stepped, defected or chiral surface. The surface may be cut to achieve a stepped, defected or chiral surface. Such a stepped surface will enhance the energy difference due to the chiromagnetic effect which will be further enhanced by the present of a magnetic field and forms a method of preferentially aligning molecules in particular directions The present invention is also applicable to chiral sensors and to analytical instruments. Such a device is envisaged whereby, using methods similar to those outlined for molecular wires and nanopatterning a surface is constructed with a specific array of different enantiomers or one enantiomer. Each area of the surface is connected to microcircuits such that changes in local fields can be sensed electronically or magnetically. A dose of a subsequent target chiral molecule is applied which will bond, chemically or physically, to structurally or electronically affect the original adsorbed enantiomer. Such changes are normally very small but are enhanced by the surface chiro-magnetic effect allowing a target molecule to be sensed. A micro sensor is thereby provided for small quantities of chiral molecules.

Manipulation of magnetic fields, enantiomers selected, concentration, and position allows single target molecules or racemic mixtures to be sensed. Alternatively a difference in the magnetic field may be sensed by virtue of the presence of a chiral molecule affecting local magnetic fields.

These devices can be constructed for detecting specific molecules e.g., in proteomics.

The devices described above allow a patterned surface of many different enantiomers to be positioned in a specific array. The introduction of a mixture of unknown molecules in the gas or liquid phase will result in preferential adsorption according to chemical structure. Using sensor technology previously described this allows the detection of particular types of molecule and hence forms the basis of an analytical instrument.

In order to utilize the chiromagnetic effect for separations and heterogeneous catalysis the surface of the selected substrate can be structured. Chiral molecules on chirally cut surfaces are known to have very slightly different desorption energies [38]. An example of a chirally cut surface is Nickel [643]. FIG. 9 illustrates the atomic arrangements in S and R forms of chirally cut nickel.

This very small energy difference is amplified by the chiro-magnetic effect whereby the applied magnetic field forces one enantiomer to take up an alignment which in unfavorable with respect to the chirally cut surface. This situation allows separation of a racemic mixture whereby one enantiomer is separated by virtue of a different desorption energy.

Similarly the same technology can be used to enhance the known energy differences on chirally cut surfaces using a magnetic field to perform heterogeneous catalysis of chiral reactions. In a magnetized area a specific reaction is favored over another by virtue of an enhanced energy difference.

Applications of the present invention to coatings and barriers will now be considered. The methods previously described allow the deposition of a specific pattern of enantiomers on a surface. Such a coated surface will have a range of properties that are different from the original surface and may be made to be variegated along a surface. Alternatively as previously described further docking molecules may be deposited onto the enantiomers. Such technology allows the development of highly specific surface coatings with biological, chemical or pharmaceutical application.

Applications of the present invention to logic devices including memories and processors are of particular importance.

A device is envisaged whereby an enantiomer is deposited on a surface which is magnetized. Each single chiral molecule writes on the surface on a length scale of 1 nm thus bringing data storage density to the order of terabit per square centimeter. The magnetization and spins of the surface influence and are in turn influenced by the adsorption of the chiral molecule. So, firstly the chirality of the molecule dictates which surface spin/electronic states are involved in the adsorption process and the specific orientation of the molecule in the field. Therefore, this enables the chiral molecule to encode a new class of nanomagnetic structures. Secondly, while the invention could be utilised in conventional binary logic systems, the writing code can be advanced from the standard binary (0,1) to ternary(0,1,−1) where 0 refers to no adsorption, 1 refers to adsorption of one enantiomer and −1 refers to the adsorption of the mirror enantiomer.

Adsorption can be carried out randomly from for example the gas phase or at a selected site (e.g., via STM manipulation) which would deliver a molecule to a specific site. Such technology has been demonstrated previously [39]. Given the chiromagnetic effect described in this patent each enantiomer will adopt a different orientation subject to its chirality. This allows reading, writing and erasure to be increased beyond 0<->1 to 0<->1 or −1 and critically from 1<->−1.

These local magnetic structures can be created by gas phase or liquid phase adsorption which are then read at the nanoscale using well understood standard Scanning Tunneling Microscopic devices such as spin polarized STM or GMR heads (giant magneto resistance). Alternatively, STM manipulation can be used to adsorb or desorbed a molecule on a selective site. In addition switching from 1 to −1 can be achieved by changing the local magnetization using STM technology as an example.

A number of potential data storage devices have been constructed on a nanoscale previously for example using STM assisted chemical vapor deposition. However, the use of the chiromagnetic effect allows a novel approach to data storage and also the creation of a second hierarchy of storage. In particular this technology will allow an advance from electronic devices to chiral electronic devices and from spintronic devices to chiral spintronic devices.

REFERENCES

All the documents below are incorporated herein by reference either in respective entireties or in the respective portions cited below.

[1] Symmetry 2000, Part 1, Chapters 24-27. Ed. 1 Hargittai and T. C. Lautrent, Portland Press, London 2002.
[2] Izumi Y., *Adv. Catal.* 1983, 32, 215.
[3] Tai, A.; Harada, T. In Tailored Metal Catalysts (ed. Y. Iwasawa) D. Reidel Publishing Company, 1986, 265.
[4] Tai A.; Harada T.; Hiraki Y.; Murakami S. *Bull. Chem. Soc. Jpn.* 1983, 6, 1414.
[5] Baiker, A.; Blaser, H. U. in Handbook of Heterogeneous Catalysis, (eds G. H. Ertl, H. Knoezinger, & J. Weinheim) VCH, New York 1997, 5, 2422.
[6] Blaser, H. U.; *Tetrahedron; Asymmetry,* 1991, 2, 843.
[7] Baiker, A.; *Current Opinion in Solid State and Materials Science* 1998, 3, 86.
[8] Webb G.; Wells P. B. *Catal. Today* 1992, 12, 319.
[9] Keane M. A.; Webb G. J. *Catal.* 1992, 136, 1.
[10] S. Barlow and R. Raval, Surface Science Reports 298 (2003) 1.
[11] Ortega Lorenzo, M.; Baddeley, C. J.; Muryn, C.; Raval, R. *Nature* 2000, 404, 376.
[12] Ortega-Lorenzo M.; Haq S.; Bertrams T.; Murray P.; Raval R.; Baddeley C. J. *J Phys. Chem.* 1999, 103 10661.
[13] Williams J.; Haq S.; Raval R. *Surf. Sci.* 1996, 368, 303.
[14] Raval R.; Baddeley, C. J.; Haq, S.; Louafi, S.; Murray, P.; Muryn, C.; Ortega Lorenzo, M.; Williams, J. *Studies in Surf, Sci Catal.* 1999, 122, 11.
[15] Raval, R. *CATTECH* 2001, 5, 12.
[16] Ernst, K. -H. ; Neuber, M.; Grunze, M.; Ellerbeck, U. *J. Am. Chem. Soc.* 2001, 123, 493.
[17] De Feyter, S.; Gesquiere, A.; Abdel-Mottaleb, M. M.; Grim, P. C. M.; De Shryver, F. C.; Meiners, C.; Sieffert, M.; Valiyaveettil, S.; Mullen, K, *Accounts of Chemical Research A* 2000, 33, 520.
[18] Schunack, M.; Laegsgaard, E.; Stensgaard, I.; Johannsen, I.; Besenbacher, F. *Agnew. Chem. Int. Ed.* 2001, 40, 2623.
[19] V. Humblot, S. Haq, C. Muryn, W. A. Hofer and R. Raval, *J. Am. Chem. Soc.,* 124 (2002) 503.
[20] A. Kuhnle, T. R. Lineroth, B. Hammer and F. Besenbacher, Nature, 415 (2002) 891.
[21] G. L. J. A. Rikken, E. Raupach, Nature, Vol. 405, No. 6789 (2002), 932-935.
[22] G. L. J. A. Rikken. E. Raupach, Nature, Vol. 309(1997) 493-494.
[23] M. F. Lin, Physica B., Vol 269, No. 1 (1999), 43-48.

[24] M. Minguet, Dominique Luneau, E. Lhotel, V. Villar, C. Paulsen, D. B. Amabilino and J. Veciana, Agnew. Chem. Int. Ed. Vol. 41, No. 4 (2002), 586-589.

[25] M. Minguet, D. B. Amabilino, J. Cirujeda, K. Wurst, I. Mata, E. Molina, J. J. Nova and J. Veciana, Chem. Eur. J., Vol. 6, No. 13 (2002), 2350-2361.

[26] J. Carmeli et al., Agnew. Chem. Int. Ed., 41 (2002) 761.

[27] R. F. Service, Science, Vol. 295 (2002), 2398-2399.

[28] D. Malakoff and R. F. Service, Science, Vol. 294 (2001), 2442-2443.

[29] D. Ruiz, Z. Sun, B. Albela, K. Folting, J. Ribas, G. Christou and D. N. Hendrickson, Agnew. Chem. Int. Ed., Vol. 37, No. 3(1998), 3002-302.

[30] I. Ratera, D. Ruiz-Molina, J. Vidal-Gancedo, K. Wurst, N. Daro, J-F Letard, C. Rovira and J. Veciana, Agnew, Chem. Int. Ed. Vol. 40, No. 5 (2001), 919-922.

[31] J. C. Goodwin, R. Sessoli, D. Gattaschi, W. Wernsdorf, A. K. Powell and S. L. Heath, J. Chem. Soc., Dalton Trans., (2002), 1935-1840.

[32] D. Ruiz-Molina, P. Gerbier, E. Rumberger, D. B. Amabilino, I. A. Guzei, K. Folting, J. C. Huffman, A. Rheingold, G. Christou, J. Veciana and D. N. Hendrickson, J. Mater. Chem., Vol. 12 (2002), 1152-1161.

[33] A. Caneschi, D. Gatteschi, N. Lalioti, C. Sangregorio and R. Sessoli, J. Chem. Soc., Dalton Trans., (2002), 3907-3912.

[34] D. Gatteschi, R. Sessoli and A. Cornia, Chem. Commun., (2002), 725-732.

[35] R. Sessoli, D. Gatteschi, A. Caneschi and M. A. Novak, Nature, Vol. 365 (1993), 141-143.

[36] L. Thomas, F. Lionti, R. Ballou, D. Gatteschi, R. Sessoli and B. Barbara, Nature, Vol. 383 (1996), 145-147.

[37] D. M. Eigler and E. K. Schweizer, Nature 344 (1990) 424.

[38] A. J. Gellman, J. D. Horwarth and M. T. Benlow, L. Molecular Catalysis A, 167 (2001) 1.

[39] J. Shen, J. Kirschner, Surface Science, Article in Press, (2001).

While the foregoing is directed to embodiments of the present invention, other and further embodiments of the invention may be devised without departing from the basic scope thereof, and the scope thereof is determined by the claims that follow.

What is claimed is:

1. A device comprising chiral molecules and one of a surface and an interface, formed by material having one of a crystalline, a nanocrystalline and a nanoparticulate structure at which the chiral molecules are adsorbed, wherein the adsorbed molecules are influenced by their magnetic environment in a manner which is different for different enantiomers thereof.

2. The device as claimed in claim 1, further comprising: means for controlling the magnetic environment of the adsorbed molecules and thereby controlling behavior of the chiral molecules.

3. The device as claimed in claim 1, further comprising: means for adjusting the magnetic environment of the adsorbed molecules and thereby adjusting at least one property of the chiral molecules.

4. The device as claimed in claim 1, further comprising: at least one of a magnet, electromagnet and other means for applying a magnetic field at one of the surface and the interface to influence the adsorbed molecules.

5. The device as claimed in claim 4 wherein the one of the surface and the interface comprises material which is capable of being magnetized.

6. The device as claimed in claim 5 wherein a magnetic field is provided by virtue of magnetization of material forming the one of the surface and the interface.

7. The device as claimed in claim 1 wherein orientation of the adsorbed molecules is controlled by application of a magnetic field.

8. The device as claimed in claim 1 wherein the chiral molecules comprise two different enantiomeric forms of the same molecule.

9. The device as claimed in claim 1 wherein two different enantiomers are adsorbed at the one of the surface and the interface in orientations which are asymmetric with respect to one or more mirror planes of the one of the surface and the interface.

10. The device as claimed in claim 1 wherein one enantiomer of the chiral molecules is preferentially adsorbed.

11. The device as claimed in claim 1 wherein one enantiomer of the chiral molecules is preferentially adsorbed and the preferential adsorption of the different enantiomers is controlled by controlling their magnetic environment.

12. The device as claimed in claim 1 wherein, by changing the magnetic environment of chiral molecules adsorbed at the one of the surface and the interface, movement of the adsorbed molecules is produced in situ.

13. An apparatus, comprising:
a substrate providing one of a surface and an interface;
means for providing a magnetic field at the one of a surface and an interface; and
means for supplying chiral molecules for adsorption at the one of the surface and the interface, the adsorbed molecules being influenced by the magnetic field in a manner which is different for different enantiomers thereof, wherein the molecules for adsorption are provided in one of a liquid phase and a gas phase.

14. An apparatus, comprising:
a substrate providing one of a surface and an interface;
means for providing a magnetic field at the one of a surface and an interface; and
means for supplying chiral molecules for adsorption at the one of the surface and the interface, the adsorbed molecules being influenced by the magnetic field in a manner which is different for different enantiomers thereof, wherein the molecules for adsorption are provided by one of sublimation and evaporation.

15. The device as claimed in claim 1, further comprising a substrate for providing the one of a surface and an interface, wherein magnetization of the substrate contributes to the magnetic environment.

16. The device as claimed in claim 1, further comprising a substrate for providing the one of a surface and an interface, and at least one of a magnet, an electromagnet and other means for applying a magnetic field, wherein the magnetic field is formed separately from the substrate.

17. The apparatus as claimed in claim 13 wherein the substrate is contained in an envelope in which controlled conditions are provided.

18. The apparatus as claimed in claim 16, further comprising:
means for adjusting at least one of a position and an orientation of the substrate relative to the magnetic field.

19. An apparatus, comprising:
a substrate providing one of a surface and an interface;
means for providing a magnetic field at the one of a surface and an interface;
means for supplying chiral molecules for adsorption at the one of the surface and the interface, the adsorbed molecules being influenced by the magnetic field in a manner which is different for different enantiomers thereof; and means for locally heating the substrate to cause local desorption of chiral molecules therefrom.

20. An apparatus, comprising:
a substrate providing one of a surface and an interface;
means for providing a magnetic field at the one of a surface and an interface;
means for supplying chiral molecules for adsorption at the one of the surface and the interface, the adsorbed molecules being influenced by the magnetic field in a manner which is different for different enantiomers thereof; and
means for locally heating the substrate to cause local desorption of chiral molecules therefrom, wherein the means for locally heating the substrate comprises at least one heating element disposed at one of within the substrate and adjacent the substrate.

21. An apparatus, comprising:
a substrate providing one of a surface and an interface;
means for providing a magnetic field at the one of a surface and an interface;
means for supplying chiral molecules for adsorption at the one of the surface and the interface, the adsorbed molecules being influenced by the magnetic field in a manner which is different for different enantiomers thereof; and
means for causing the adsorbed molecules to form a controlled pattern.

22. The apparatus as claimed in claim 21, wherein the pattern is a nanopattern.

23. The apparatus as claimed in claim 21, further comprising:
means for controlling a magnetic field for creating the controlled pattern.

24. The apparatus as claimed in claim 21, further comprising:
means for applying a magnetic field having a field strength which varies along the substrate to create pattern in the adsorbed chiral molecules.

25. The apparatus as claimed in claim 21, further comprising:
means for providing a concentration gradient of chiral molecules along the substrate during dosing of the molecules, thereby creating a pattern in the adsorbed chiral molecules.

26. An apparatus, comprising:
a substrate providing one of a surface and an interface;
means for providing a magnetic field at the one of a surface and an interface; and
means for supplying chiral molecules for adsorption at the one of the surface and the interface, the adsorbed molecules being influenced by the magnetic field in a manner which is different for different enantiomers thereof, wherein the substrate provides one of a stepped, defected and chiral surface for adsorption of the chiral molecules, upon which a chosen enantiomer is one of preferentially aligned and preferentially adsorbed.

27. An apparatus, comprising:
a substrate providing one of a surface and an interface;
means for providing a magnetic field at the one of a surface and an interface; and
means for supplying the racemic mixture to the one of a surface and an interface, wherein one enantiomer is preferentially adsorbed or desorbed relative to another.

28. A logic device, comprising:
a substrate providing one of a surface and an interface;
means for providing a magnetic field at the one of a surface and an interface; and
means for supplying chiral molecules for adsorption at the one of a surface and an interface thereby to encode logic states.

29. The device as claimed in claim 28, wherein the chiral molecules are utilized to encode three different logic states corresponding respectively to a presence of one enantiomer, a presence of another enantiomer and an absence of either.

30. The device as claimed in claim 28, wherein two enantiomers adopt different orientations at the one of the surface and the interface, by virtue of which the device is readable.

31. The device as claimed in claim 28, wherein an applied field is utilized to alter orientation of chiral molecules to switch logic states.

32. A heterogeneous catalysis apparatus, comprising:
a substrate providing a surface or interface;
means for providing a magnetic field at one of a surface and an interface; and
means for supplying chiral molecules for adsorption at the one of the surface and the interface, the adsorbed molecules being influenced by the magnetic field in a manner which is different for different enantiomers thereof.

33. The apparatus as claimed in claim 32 utilizing selective adsorption of different enantiomers at the one of the surface and the interface.

34. The device as claimed in claim 1 in which the chiral molecules form one of a coating and a barrier.

35. The device as claimed in claim 1 which is a sensor for detecting a chosen enantiomer.

36. A sensor for detecting a chosen enantiomer, comprising:
an array of chiral molecules adsorbed at one of a surface and an interface, the chiral molecules being chosen to receive a target enantiomer; and
means for detecting the presence of the target enantiomer.

37. The device as claimed in claim 1 wherein the one of the surface and the interface is one of stepped, defected and chiral.

38. A method, comprising:
controlling at least one property of chiral molecules adsorbed at one of a surface and an interface by controlling a magnetic environment of the molecules, wherein an effect of the magnetic environment is to alter an orientation of different enantiomeric forms of the chiral molecules by angles which are unequal.

39. The method as claimed in claim 38 wherein an influence of the magnetic environment is of different magnitude for different enantiomers.

40. The method as claimed in claim 38, further comprising:
providing a magnetic field at the one of the surface and the interface to control orientation of the chiral molecules.

41. The method as claimed in claim 38 wherein magnetization of a substrate forming the one of the surface and the interface contributes to a magnetic field at the one of the surface and the interface.

42. The method as claimed in claim 38, further comprising:
providing a magnetic field utilizing one of a magnet and an electromagnet.

43. The method as claimed in claim 38, further comprising:
  causing rotational movement to the adsorbed molecules in situ by changing their magnetic environment.

44. The method as claimed in claim 38, further comprising:
  providing a magnetic field at the one of the surface and the interface; and
  supplying chiral molecules for adsorption at the one of the surface and the interface.

45. The method as claimed in claim 38, further comprising: forming a controlled pattern in the adsorbed molecules.

46. The method as claimed in claim 45, further comprising:
  controlling an applied magnetic field to create the controlled pattern.

47. The sensor of claim 38, wherein the array of chiral molecules is coupled to microcircuitry for detection of local fields in the array, and the means for detecting the presence of the target enantiomer includes the microcircuitry.

48. The apparatus as claimed in claim 27 which is for separation of racemic mixtures.

49. The apparatus as claimed in claim 21, wherein the one of the surface and the interface is one of stepped, defected and chiral.

50. The apparatus as claimed in claim 27, wherein the one of the surface and the interface is one of stepped, defected and chiral.

51. The apparatus as claimed in claim 32, wherein the one of the surface and the interface is one of stepped, defected and chiral.

52. The sensor as claimed in claim 36, wherein the one of the surface and the interface is one of stepped, defected and chiral.

53. The method as claimed in claim 38, wherein the one of the surface and the interface is one of stepped, defected and chiral.

54. The device as claimed in claim 1, wherein the adsorbed molecule affects the surface spin states in a manner that is related to the chirality of the molecule.

55. The apparatus as claimed in claim 13, wherein the adsorbed molecule affects the surface spin states in a manner that is related to the chirality of the molecule.

56. The apparatus as claimed in claim 14, wherein the adsorbed molecule affects the surface spin states in a manner that is related to the chirality of the molecule.

57. The apparatus as claimed in claim 21, wherein the adsorbed molecule affects the surface spin states in a manner that is related to the chirality of the molecule.

58. The device as claimed in claim 28, wherein the adsorbed molecule affects the surface spin states in a manner that is related to the chirality of the molecule.

59. A method of locally manipulating magnetization of a body providing a surface, the method comprising adsorption of chiral molecules upon the surface.

60. The method as claimed in claim 59, wherein the adsorbed molecule affects the surface spin states in a manner that is related to the chirality of the molecule.

61. The method as claimed in claim 59, further comprising controlling the location of the adsorbed molecules upon the surface.

62. The method as claimed in claim 61, wherein control of the location of the adsorbed molecules is by manipulation of an applied magnetic field.

63. The method as claimed in claim 61, wherein control of the location of the adsorbed molecules is by localised heating of the body.

64. The method as claimed in claim 61, wherein control of the location of the adsorbed molecules is by STM manipulation.

65. The method as claimed in claim 61, wherein control of the location of the adsorbed molecules involves the surface being any of (a) stepped (b) defected and (c) chiral.

66. A device comprising:
  a body providing a surface;
  chiral molecules adsorbable upon the surface; and
  means for controlling adsorption of the molecules on the surface to thereby manipulate magnetization of the body.

67. The device as claimed in claim 66, wherein the surface is one of stepped, defected and chiral.

68. The device as claimed in claim 66, wherein the adsorbed molecule affects the surface spin states in a manner that is related to the chirality of the molecule.

69. The device as claimed in claim 66, further comprising an arrangement for localising the adsorption of the chiral molecules.

70. The device as claimed in claim 69, which is for one of nanopatterning and lithography.

71. The device as claimed in claim 69, which is one of an analytical instrument and a sensor.

72. A method of enantiomer selection in a racemic mixture, comprising:
  providing at least one of a magnetized non-chiral surface and interface; and
  selectively adsorbing or desorbing the racemic mixture by exposing the racemic mixture to the at least one of the non-chiral surface and the interface, wherein the enantiomer selection is facilitated by interactions between the racemic mixture and the at least one of the non-chiral surface and the interface.

73. A separation medium for separating different enantiomeric forms of a chiral molecule, comprising a non-chiral surface upon which at least one enantiomer is adsorbable, the rates of adsorption of the different enantiomers being different, wherein the separating the different enantiomeric forms is facilitated by interactions between the non-chiral surface and the at least one enantiomer.

74. A device for enantiomer selection in a racemic mixture of chiral molecules, the device comprising a non-chiral surface or interface at which the chiral molecules are adsorbed, wherein one enantiomer is preferentially adsorbed and adsorption of the chiral molecules is facilitated by interactions between the non-chiral surface and the chiral molecules.

75. A logic device comprising a body providing surface wherein the logic device has chiral molecules adsorbed to the body providing surface.

76. The logic device as claimed in claim 75 which is a memory.

77. The logic device as claimed in claim 75 in which chiral molecules serve to switch spin states of the body and the spin states are interpreted as logic states.

78. The device as claimed in claim 77, wherein the adsorbed molecule affects the surface spin states in a manner that is related to the chirality of the molecule.

79. The logic device as claimed in claim 75 in which one of position and orientation of chiral molecules adsorbed upon the surface is interpreted as a logic state, the device being adapted to switch enantiomer position or orientation.

80. A method of sensing magnetization states of a surface or interface, comprising adsorption of chiral molecules at the surface or interface and sensing of at least one of the presence and the orientation of the adsorbed molecules.

81. A method of nanopattering or lithography comprising adsorption of chiral molecules at a surface or interface and controlling a local magnetic field to control said adsorption.

82. The method as claimed in claim 81, wherein the adsorbed molecule affects the surface spin states in a manner that is related to the chirality of the molecule.

* * * * *

UNITED STATES PATENT AND TRADEMARK OFFICE
CERTIFICATE OF CORRECTION

PATENT NO.        : 7,258,236 B2                                  Page 1 of 1
APPLICATION NO. : 10/996262
DATED             : August 21, 2007
INVENTOR(S)       : Rasmita Raval It is certified that error appears in the above-identified patent and that said Letters Patent is hereby corrected as shown below:

Column 8, Line 9, please delete "desorbed" and insert --desorb--;

Column 9, Line 4, please delete "arrangements" and insert --arrangement--;

Column 12, Line 6, please delete "desorbed" and insert --desorb--;

Column 17, Line 17, in Claim 47, please delete "38" and insert --36--.

Signed and Sealed this

Fifth Day of May, 2009

JOHN DOLL
*Acting Director of the United States Patent and Trademark Office*